United States Patent [19]

Kwan et al.

[11] Patent Number: 5,660,978
[45] Date of Patent: Aug. 26, 1997

[54] STABILIZATION OF ANALYTES

[75] Inventors: Shing Fai Kwan, Ventura, Calif.; Ivan E. Modrovich, 96 Natalie Way, Camarillo, Calif. 93010; Rebecca Jolene Hunt, Carpinteria, Calif.

[73] Assignee: Ivan E. Modrovich, Camarillo, Calif.

[21] Appl. No.: 483,375

[22] Filed: Jun. 7, 1995

Related U.S. Application Data

[63] Continuation of Ser. No. 956,838, Oct. 5, 1992, which is a continuation of Ser. No. 382,425, Jul. 19, 1989, abandoned.

[51] Int. Cl.$^6$ .................................................. C12Q 1/70
[52] U.S. Cl. .......................... 435/5; 435/188; 436/8; 436/16; 436/18; 436/512; 436/176; 436/826
[58] Field of Search ........................ 435/5, 188; 436/512, 436/8, 16, 18, 176, 826

[56] References Cited

U.S. PATENT DOCUMENTS

| | | |
|---|---|---|
| 4,157,280 | 6/1979 | Halbert et al. . |
| 4,267,272 | 5/1981 | Josephson . |
| 4,652,524 | 3/1987 | Modrovich . |

OTHER PUBLICATIONS

Sternberger et al., "The unlabeled antibody enzyme method of immunohistochemistry," *J. Histochem. Cytochem.* 18: 315–333 (1970).

Sawada et al., "Human prostatic acid phosphatase (EC–3.1.3.24) Stabilization of prostatic acid phosphatase against thermal inactivation by the homologous antibody," *Chem Pharm Bull* (Tokyo) 29:2935–2939 (1981), abstract only.

Cheridnickova et al., "Evidence for the stabilizing effect of antibodies on the subunit association of glyceraldehyde–3–phosphate dehydrogenase," *Mol. Immunol.* 18: 1055–1064 (1981), abstract only.

Melchers et al., "Enhanced stability against heat denaturation of E. coli wild type and mutant β–galactosidase in the presence of specific antibodies," *Biochem. Biophys. Research Comm.* 40: 570–575 (1970).

Boyd et al., *Fundamentals of Immunology*, Third Edition (Interscience Publishers, Inc., New York) pp. 318–326 (1956).

Mason et al., "Preparation of peroxidase:Antiperoxidase (PAP) complexes for immunohistological labeling of monoclonal antibodies," *J. Histochem. Cytochem.* 30:1114–1122 (1982).

*Primary Examiner*—Christine M. Nucker
*Assistant Examiner*—Jeffrey Stucker
*Attorney, Agent, or Firm*—Christie, Parker & Hale, LLP

[57] ABSTRACT

A method for stabilizing analytes with antibodies and antibody fragments comprises dissolving the analyte in a liquid to form a solution, adding analyte-specific antibodies, fragments of such antibodies, or both to the solution, heating the solution, and then cooling and filtering the solution. The filtered solution may be diluted in a suitable matrix.

39 Claims, No Drawings

STABILIZATION OF ANALYTES

CROSS-REFERENCE TO RELATED APPLICATION

This is a continuation of application Ser. No. 07/956,838, filed Oct. 5, 1992, which is a continuation of Ser. No. 07/382,425, filed Jul. 19, 1989, now abandoned.

BACKGROUND OF THE INVENTION

The physiological activity of many macromolecular biomolecules depends upon their tertiary and secondary structures, as well as their primary structures. Molecules with fibrous, globular, and other structures are known. Deconvolution of conformational features of a macromolecule (e.g., an enzyme) can significantly reduce or even destroy the molecule's activity. Changes in the tertiary structure of a macromolecule can be caused by heat, strong acids or bases, and other conditions.

The use of enzymes, hormones, and other biomolecules in both clinical and research capacities is well established. Such compounds are often difficult to isolate and expensive to manufacture. It is desirable to protect these and other analytes from denaturation, degradation, and other processes that destroy physiological activity.

The medical and research communities have exploited the interaction between antibodies and antigens for a variety of detection methodologies for over 30 years. Common techniques include tissue staining, radioimmunoassaying, enzyme immunoassaying, fluorescence immunoassaying, and immunoelectrophoresis. In each case, the unique ability of an antibody to bind specifically to a particular antigen is exploited.

An antibody may be broadly defined as a globular protein formed in response to the introduction of an antigen. Antibodies have molecular weights of about 160,000, and may be produced by monoclonal and polyclonal techniques.

An antigen may be defined as a substance which reacts with the products of specific humoral or cellular immunity; in other words, antigens are substances that react in a specific manner with antibodies. Numerous types of natural and synthetic antigens are known, including proteins, carbohydrates, nucleic acids, and lipids. Antibodies themselves can act as antigens. Haptens are small molecules that can react with specific antibodies, but do not elicit specific antibody production unless injected in a conjugated form. In other words, the hapten must be conjugated to a high molecular weight carrier such as bovine serum albumin.

An antibody has two functionally distinct regions, called the "variable" region, and the "constant" region, respectively. The variable region can bind to an antigen without the formation of covalent chemical bonds. The constant region can associate with cellular receptors. Differences in the molecular make-up of the constant regions define particular classes and subclasses of immunoglobulins. There are five principal classes, denoted in the art as IgG, IgA, IgM, IgD and IgE, with IgG being the most prevalent.

A given antibody can react only with its homologous antigen, or with an antigen of similar molecular structure. In contrast, a given antigen may interact with more than one type of antibody. A "key-lock" analogy is often used to describe the interaction; the antigen resembles a key which precisely fits an antibody's corresponding structural shape, or "lock." Non-covalent binding stabilizes the complex and holds it together.

The antigen-antibody interaction is primarily a result of three forces: van der Waal's and London forces (dipole-dipole interactions), hydrophobic interactions, and ionic (coulombic) bonding.

SUMMARY OF THE INVENTION

The present invention provides a process for the stabilization of antigens ("analytes" herein) in a liquid medium, utilizing the unique properties of antibodies. The invention thus provides stabilized analyte preparations which have desirable. processing characteristics (e.g., the ability to be aseptically filtered). The process comprises binding antibodies or antibody fragments to proteins, enzymes, and other analytes, to prevent the spontaneous folding or unfolding of, e.g., peptide chains within the analyte. Additionally, the bounding antibody or antibody fragment shields the analyte (including enzymes) from proteolytic enzymes and various oxidizing compounds. The antibody-stabilized analytes retain their bioactivity.

In a preferred embodiment of the invention, a stabilized analyte is prepared by adding the analyte in a saline solution, then adding antibodies or antibody fragments to the solution. The solution is preferable agitated and heated, and then cooled and filtered. The filtered solution is then diluted into a defined matrix of desirable concentration. The solution is assayed for antibody-stabilized analyte activity during and after the preparation of the stabilized complex.

DETAILED DESCRIPTION

As used herein, the term "analyte" refers to a macromolecule that can provide or coact with an antigen. Examples include peptides, proteins, glycoproteins, lipoproteins, enzymes, carbohydrates, and nucleic acids. More particularly, the following enzymes are representative of some of the analytes which may be stabilized with the present invention: prosthetic acid phosphatases, aspartate aminotransferases, alanine aminotransferases, amylases, malate dehydrogenase, ureases, hexokinases, glucose-6-phosphate dehydrogenases, peroxidases, creatine kinases, glutamate dehydrogenases, and alkaline phosphatases. Hereinafter, "antigen" shall mean antigens and the functional parts of such antigens.

In accordance with the present invention, an analyte is stabilized by first dissolving the analyte in an appropriate solvent. Enzymes, antibodies, and other globular proteins are typically soluble in water or aqueous solutions of acids, bases or salts. Other analytes may be solvated in aqueous or nonaqueous solutions. Preferably a 0.5% to 30% saline solution is used.

Once a solution of the analyte has been prepared, a predetermined amount of antibodies is added to the analyte solution. More than one type of the antibody may be added. The antibodies used in the present invention may be prepared, isolated, and purified by a variety of methods that will be understood by those skilled in the art. Stabilized analyte solutions can be prepared with monoclonal and polyclonal, antibodies. For example, polyclonal antibodies may be produced by injecting the analyte of interest into a host mammal, thereby inducing an antigenic response that results in antibody formation. After bleeding the mammal, standard fractionation procedures are used to isolate various types of antibodies, each of which is specific to the particular analyte. The antibodies so produced can be combined with the analyte to yield a stabilized analyte-antibody complex. Mammals include rats, mice, primates, goats, sheep, rabbits, cows, horses and the like.

After an analyte-antibody solution is prepared, the solution is agitated and heated for a period of time sufficient to allow formation of a stabilized analyte-antibody complex. Depending on the system equilibrium may be reached in seconds, hours, or days. Typically the analyte-antibody solution is heated for several minutes to several hours, at temperatures of ambient to about 65° C. In addition to accelerating the formation of a stabilized analyte-antibody complex, elevated temperatures reduce or even eliminate instable enzymatic activity of the solution.

After a stabilizing amount of time has passed, the analyte-antibody solution may then be cooled, filtered, and assayed for analyte content. Filtration may be accomplished by passing the equilibrated solution through a suitable size control device, such as a filter, molecular sieves, resins, hollow fibers, and spiral cartridge exclusions. Preferably, a 0.2 micron aseptic filter is used. If desired, the filtered solution may be diluted by adding the solution to a matrix which may be a chemical reagent, a buffered solution, a salt solution, protein solution, polymer solutions and mixtures thereof. A presently preferred protein matrix solution essentially consists of a stabilized preparation of mammalian serum, such as human, bovine, equine, porcine, rabbit serum and the like components, or mixtures thereof. The antibody-stabilized analyte is used to adjust the activity by diluting into protein matrix as desired. The protein solution may be heated, cooled and filtered as desired.

It has been found that certain analytes tend to form insoluble immunocomplexes when allowed to react with whole antibody molecules, in part because of the generally divalent nature of most antibodies. Immunocomplexes have extremely high molecular weights, may be insoluble, and may be unsuited for processing techniques such as aseptic filtration.

Accordingly, in a preferred embodiment of the invention, antibody Fab fragments or mixtures of whole antibodies and Fab fragments are added to the analyte solution. Because Fab antibody fragments are monovalent, formation of insoluble immunocomplexes is avoided, and the benefits of stabilization and filterability are achieved.

The fragmentation of antibodies may be accomplished in a number of ways.[1] A preferred method is papain hydrolysis using enzymes such as papain. Papain (also called papayotin) is an enzyme with substantial thermostability. It is capable of "digesting" or fragmenting protein molecules. Treatment of an antibody with papain in an aqueous medium yields three antibody fragments: two "Fab" fragments and one "Fc" fragment. Fc denotes a fragment which includes the "constant" region of the molecule.

[1] "Handbook of Experimental Immunology," Stanworth and Turner, D. W. Weir 2nd Ed. 1973, Blackwell Scientific Publication, Oxford (incorporated herein by reference).

Each Fab fragment possesses one antigen-combining site (the "variable" region), and may combine with an antigen in a manner similar to a whole molecule antibody. In contrast, the Fc fragment often lacks antigen-binding capability, but retains many antigenic and biological properties of the parent antibody.

EXAMPLE 1

Preparation of stabilized Human Prosthetic Acid Phosphatase (ACP)

Stabilized ACP was prepared as follows:

ACP was added to 10 ml of 0.9% NaCl at 4° C. to yield an ACP concentration of 877 IU. 6 mg of Fab was added to the solution. Here, "Fab" denotes antibody fragments the solution. Here, "Fab" denotes antibody fragments formed by papain hydrolysis of various polyclonal antibodies. The antibodies were formed in response to an ACP-induced antigenic response in a host mammal.

The solution was rocked at room temperature for four hours. 4.8 mg of IgG was then added to the solution. Here, "IgG" denotes whole molecule polyclonal antibodies prepared as described above.

The solution was rocked overnight at room temperature, then heated for 36 minutes at 56° C.

The solution was cooled at 4° C., and filtered through a 0.2 micron filter.

The filter solution was assayed for ACP, using conventional techniques.

The filtered solution was diluted by adding a protein matrix, heated at 57° C. for 30 minutes, and then cooled to 4° C.

The solution was again filtered through a 0.2 micron filter.

Enzymatic activity of stabilized ACP prepared in the above manner is shown in Table 1. The stability studies were conducted at different temperatures. The results show that enzymatic activity remained high even after three days at elevated temperatures. The control solution had an ACP concentration of 1.00 IU at time 0° at 4° C.

TABLE 1

Accelerated Stability of Stabilized ACP

| Pilot | Activity of ACP (in IU) after solutions were stored at 72 hours at temperature shown | | |
|---|---|---|---|
| | 4° C. | 41° C. | 47° C. |
| Stabilized | 1.23 | 1.32 | 1.00 |
| Control Untreated | 0.20 | 0 | 0 |

The results of long term stability studies, carried out at lower temperatures, are shown in Table 2. ACP activity remained even after 71 days. "RT" denotes room temperature.

TABLE 2

Accelerated Stability of Stabilized ACP

| Storage time in day/ Storage Temp | 6 | 13 | 27 | 41 | 56 | 71 |
|---|---|---|---|---|---|---|
| Stabilized | | | | | | |
| 4° C. | 1.69 | 1.79 | NA | 1.94 | NA | 1.88 |
| R.T. | 1.84 | 1.92 | 1.78 | 2.00 | 1.96 | 1.94 |
| Untreated | | | | | | |
| R.T. | 0 | NA | NA | NA | NA | NA |

EXAMPLE 2

Preparation of stabilized Calf Intestine Alkaline Phosphatase (ALP)

Stabilized ALP was prepared as follows:

ALP was added to a 0.9% NaCl solution to yield an ALP concentration of 18500 IU.

120 mg of Fab was added to 12 ml of the above solution, and the resulting solution was rocked for two hours at room temperature. The Fab was prepared by papain hydrolysis of ALP-induced polyclonal antibodies.

25 mg of IgG was added to the mixture. Here, IgG denotes whole molecule polyclonal antibodies prepared in response to an ALP-induced antigenic response in a host animal.

The mixture was rocked overnight at room temperature.

The mixture was heated at 57° C. for 35 minutes, then cooled to 4° C. and filtered through a 0.2 micron filter.

After assaying for ALP, the filtered solution was diluted to a desirable concentration by adding it to a protein matrix, heated at 57° C. for 30 minutes, and cooled to 4° C.

The stabilized solution was then filtered through a 0.22 micron filter.

The results of short-term (accelerated conditions) and long-term stability studies of stabilized ALP are shown in Tables 3 and 4 respectively.

TABLE 3

Accelerated Stability of Stabilized ALP

Activity of ALP (in IU) after solutions were stored for 6 days at temperature shown

|  | 4° C. | 41° C. | 47° C. |
|---|---|---|---|
| Stabilized | 482 | 464 | 437 |
| Untreated | 450 | 135 | 68 |

TABLE 4

Long-Term Stability of Stabilized ALP

| Storage time in day/ Storage Temperature | 6 | 13 | 27 | 41 | 56 | 71 |
|---|---|---|---|---|---|---|
| Stabilized | | | | | | |
| 4° C. | 374 | 384 | NA | 387 | NA | 387 |
| R.T. | 370 | 381 | 372 | 380 | 385 | 383 |
| Untreated | | | | | | |
| R.T. | 200 | 100 | NA | NA | NA | NA |

Stabilization of analytes in the manner described above yields preparations which resist denaturing and degrading conditions, and which retain their bioactivity for a substantial period of time.

It will be appreciated by those skilled in the art that a number of additional modifications and improvements can be made to the invention without departing from its essential spirit and scope. Accordingly, the above disclosure does not limit the invention, which is limited only by the following claims.

What is claimed is:

1. A method for stabilizing a labile protein analyte to preserve biological activity against chemical degradation in an aqueous solvent which comprises the steps of:
   (a) dissolving an analyte in an aqueous solvent selected from the group consisting of water, aqueous solutions of adds, aqueous solutions of bases and aqueous solutions of salts to form a protein analyte solution;
   (b) adding to the protein analyte solution a stabilizing amount of a soluble antibody substance to the protein analyte, said antibody substance selected from the group consisting of whole polyclonal antibodies and a mixture of whole polyclonal antibodies and polyclonal antibody fragments;
   (c) allowing stabilizing antibody substance and the protein analyte to react for a time sufficient to form a solution of an aseptically-filterable, biologically-active, stable protein analyte-antibody complex; and
   (d) aseptically filtering the biologically-active protein analyte-antibody complex, said aseptically filtered protein-antibody complex having a stability of at least 72 hours at 41° C. in an aqueous solvent for said complex.

2. A method as claimed in claim 1, wherein the solvent is a 0.5 to 30% saline solution.

3. A method as claimed in claim 1, wherein the antibodies are generated from mammalian antigenic response to the analyte.

4. A method as claimed in claim 1, in which antibody fragments are Fab fragments formed by enzymatic hydrolysis digestion of whole polyclonal antibodies.

5. A method as claimed in claim 1, wherein the analyte is selected from the group consisting of peptides, proteins, glycoproteins, lipoproteins, haptens, and mixtures thereof.

6. A method as claimed in claim 1, wherein the protein analyte is an enzyme selected from the group consisting of prosthetic acid phosphatases, aspartate aminotransferases, alanine aminotransferases, amylases, malate dehydrogenase, ureases, hexokinases, glucose-6-phosphate dehydrogenases, peroxidases, creatine kinases, glutamate dehydrogenases, and alkaline phosphatases.

7. A method is claimed in claim 1, wherein the protein analyte is an enzyme selected from the group consisting of oxidoreductases, transferases, hydrolases, lyases, isomerases, and ligases.

8. A method as claimed in claim 1, in which the mixture of protein analyte and antibody substance is heated to an elevated temperature to accelerate formation of the protein analyte antibody complex.

9. A method as claimed in claim 8, in which the elevated temperature is up to about 56° C.

10. A method as claimed in claim 1, wherein the time to form the analyte-antibody complex ranges from 1 second to several days.

11. A method as claimed in claim 1, wherein filtration is with a size control device is selected from the group consisting of filters, molecular sieves, resins, hollow fibers, and spiral cartridge exclusions.

12. A method as claimed in claim 1, wherein filtration is through a filter having a mesh size of about 0.2 micron or less.

13. A method as claimed in claim 1, further comprising the step of diluting the stabilized complex in a matrix.

14. A method as claimed in claim 13, wherein the matrix is selected from the group consisting of chemical reagents used for chemical diagnosis of biological fluids, buffered solutions, salt solutions, protein solutions, polymer solutions, human serum, and animal serum.

15. A method as claimed in claim 14, wherein the protein solution is selected from the group consisting of human proteins, non-human proteins, and mixtures thereof.

16. A method as claimed in claim 14, wherein the matrix is human or animal serum, or mixtures thereof.

17. A method for stabilizing a protein analyte against chemical degradation in an aqueous solvent to preserve biological activity of said protein analyte in a solution which comprises:
   a) dissolving at least one protein analyte which is an enzyme selected from the group consisting of prostatic acid phosphatases, aspartate aminotransferases, alanine aminotransferases, amylases, malate dehydrogenase, ureases, hexokinases, glucose-6-phosphate dehydrogenases, peroxidases, creatine kinases, glutmate dehydrogenases, alkaline phosphatases in an aqueous solvent selected from the group consisting of water, aqueous solutions of acids, aqueous solutions of bases and aqueous solutions of salts to form a protein analyte solution;

b) adding to the protein analyte solution containing the protein analyte a stabilizing amount of a soluble stabilizing antibody substance to said analyte, said antibody substance selected from the group consisting of whole polyclonal antibodies, and combinations of fragments formed by enzymatic hydrolysis of said polyclonal antibodies and said whole polyclonal antibodies;

c) allowing the stabilizing antibody substance and the protein analyte to react for a time sufficient to form a solution of an aseptically-filterable, biologically-active, protein analyte-antibody complex; and d) aseptically filtering the biologically-active protein analyte-antibody complex to form a protein-antibody complex having a stability of at least 72 hours at 41° C. in an aqueous solution of said complex.

18. A method as claimed in claim 17, in which the enzymatic hydrolysis is performed by papain.

19. A method as claimed in claim 17, in which the analyte-antibody mixture is heated to a temperature above 4° C. up to about 56° C. to accelerate formation of the analyte-antibody complex.

20. A method as claimed in claim 17, wherein the time to form the analyte-antibody complex ranges from 1 second to several days.

21. A method as claimed in claim 17, wherein filtration occurs with a filter having a mesh size of about 0.2 micron or less.

22. A method as claimed in claim 17, further comprising the step of dilution the stabilized complex in a matrix.

23. A method as claimed in claim 22, wherein the matrix is selected from the group consisting of chemical reagents used for chemical diagnosis of biological fluids, buffered solutions, salt solutions, protein solutions, polymer solutions, human serum, and animal serum.

24. A method of stabilizing a labile protein analyte to preserve against loss of biological activity by chemical degradation in the presence of water which comprises:

a) dissolving a protein analyte in a liquid solvent selected from the group consisting of water, aqueous solution of acids, aqueous solution of bases and aqueous solution of salts in which the protein analyte retains biological activity to form a protein analyte solution;

b) adding to the protein analyte solution soluble Fab fragments formed by enzymatic hydrolysis of polyclonal antibodies specific for said analyte;

c) adding soluble whole polyclonal antibodies specific for said analyte to the dissolved protein analyte solution containing the added Fab fragments, the total amount of said Fab fragments and polyclonal antibodies being added in a total amount sufficient to stabilize the protein analyte;

d) incubating the resultant protein analyte solution containing the added Fab fragments and polyclonal antibodies for a time sufficient to form an aseptically filterable solution of a protein analyte-antibody complex formed by complexing the protein analyte with the Fab fragments and polyclonal antibodies; and e) aseptically filtering the incubated stable protein analyte-antibody complex to form a filtered stabilized solution, said analyte antibody complex retaining biological activity for at least 72 hours at 41° C. in an aqueous solution of said complex.

25. A method as claimed in claim 24, in which the enzymatic hydrolysis is performed by the papain.

26. A method as claimed in claim 25, wherein the analyte is an enzyme selected from the group consisting of prostatic acid phosphatases, aspartate aminotransferases, alanine aminotransferases, amylases, malate dehydrogenase, ureases, hexokinases, glucose-6-phosphate dehydrogenases, peroxidases, creatine kinases, glutamate dehydrogenases, and alkaline phosphatases.

27. A method as claimed in claim 24, in which the analyte-antibody mixture is heated to from about ambient temperature to about 56° C. during formation of the analyte-antibody complex.

28. A method as claimed in claim 24, wherein filtration occurs using a filter having a mesh size of about 0.2 micron or less.

29. A method as claimed in claim 24, further comprising the step of adding the stabilized analyte antibody complex to a matrix.

30. A method as claimed in claim 24, wherein the matrix is selected from the group consisting of chemical reagents used for chemical diagnosis of biological fluids, buffered solutions, salt solutions, protein solutions, polymer solutions, human serum, and animal serum.

31. A method of stabilizing a protein analyte in solution wherein the biological activity of the protein analyte is preserved against chemical degradation in an aqueous solvent, which comprises:

(a) dissolving a protein analyte which is an enzyme selected from the group consisting of prostatic add phosphatases, aspartate aminotransferases, alanine aminotransferases, amylases, malate dehydrogenase, ureases, hexokinases, glucose-6-phosphate dehydrogenases, peroxidases, creatine kinases, glutamate dehydrogenases, alkaline phosphatases in a 0.5 to 30% saline solution in which the protein analyte retains biological activity to form a protein analyte solution;

(b) adding to protein analyte solution a first stabilizing antibody comprising soluble Fab fragments formed by enzymatic hydrolysis of polyclonal antibodies formed by a mammalian antigenic response to the analyte;

(c) adding to the dissolved protein analyte solution containing the added first stabilizing antibody fragments a second stabilizing soluble while polyclonal antibody substance and specific to the analyte, the total amount of added Fab fragments and whole polyclonal antibodies being sufficient to stabilize the protein analyte;

(d) incubating the resultant protein analyte solution containing the added first and second antibody stabilizing substances for a time sufficient to form an aseptically filterable solution of protein analyte-antibody complex formed by complexing the protein analyte with the first and second antibody stabilizing substances; and (e) aseptically filtering the incubated stable protein analyte-antibody complex to form a complex that is stable for at least 72 hours at 41° C. in an aqueous solution of said complex.

32. A method as claimed in claim 31, wherein the size control device is a filter having a micron mesh of about 0.2 micron or less.

33. A method as claimed in claim 31, in which the enzymatic hydrolysis is performed by the papain.

34. A method as claimed in claim 32, in which the enzymatic hydrolysis is performed by the papain.

35. A method as claimed in claim 31 in which the filtered complex is combined with a matrix is selected from the group consisting of chemical reagents used for chemical diagnosis of biological fluids, buffered solutions, salt solutions, protein solutions, polymer solutions, human serum, and animal serum heated and refiltered.

36. A method of stabilizing human prostatic acid phosphatase in solution, wherein the biological activity of the prostatic acid phosphatase is preserved against chemical decomposition, which comprises:
   (a) dissolving prostatic acid phosphatase in a 0.5 to 30% saline solution in which the prostatic acid phosphatase retains biological activity to form a protein analyte solution;
   (b) adding to the protein analyte solution containing dissolved prostatic acid phosphatase soluble Fab antibody fragments formed by papain digestion of polyclonal antibodies derived from mammalian antigenic response to prostatic acid phosphatase;
   (c) adding to the solution, containing the prostatic acid phosphatase and added Fab antibody fragments, a soluble polyclonal antibody substance formed from mammalian antigenic response to prostatic acid phosphatase to form a resultant protein analyte solution;
   (d) incubating the resultant protein analyte solution for a time sufficient to form a solution of prostatic acid phosphatase complexed with the added polyclonal antibody and polyclonal Fab antibody fragments; and
   (e) aseptically filtering the incubated stable complex to form a complex which is stable for at least 72 hours at 41° C. in an aqueous solvent for said complex.

37. A method as claimed in claim 36 in which the filtered complex is combined with a matrix is selected from the group consisting of chemical reagents used for chemical diagnosis of biological fluids, buffered solutions, salt solutions, protein solutions, polymer solutions, human serum, and animal serum and then heated and refiltered.

38. A method of stabilizing human prostatic acid phosphatase in solution, wherein the biological activity of the prostatic acid phosphatase is preserved against chemical decomposition, which comprises:
   (a) dissolving prostatic acid phosphatase in a 0.5 to 30% saline solution in which the prostatic acid phosphatase retains biological activity;
   (b) adding to the protein analyte solution containing dissolved prostatic acid phosphatase soluble Fab antibody fragments formed by papain digestion of polyclonal antibodies derived from mammalian antigenic response to prostatic acid phosphatase;
   (c) adding to the solution containing the prostatic acid phosphatase and added Fab antibody fragments, a soluble whole polyclonal antibody substance formed from mammalian antigenic response to prostatic acid phosphatase to form a resultant protein analyte solution;
   (d) incubating the resultant protein analyte solution for a time sufficient to form a solution of prostatic acid phosphatase complexed with the added polyclonal antibody and polyclonal antibody Fab fragments; and
   (e) aseptically filtering the incubated stable complex to form a complex which is stable for at least 72 hours at 41° C. in an aqueous solvent for said complex.

39. A method as claimed in claim 38 in which the filtered complex is combined with a matrix is selected from the group consisting of chemical reagents used for chemical diagnosis of biological fluids, buffered solutions, salt solutions, protein solutions, polymer solutions, human serum, and animal serum, then heated and refiltered.

* * * * *